United States Patent [19]
Chait et al.

[11] Patent Number: 5,792,664
[45] Date of Patent: Aug. 11, 1998

[54] METHODS FOR PRODUCING AND ANALYZING BIOPOLYMER LADDERS

[75] Inventors: Brian T. Chait; Rong Wang, both of New York, N.Y.; Stephen B. H. Kent, La Jolla; Steven M. Clark, Palo Alto, both of Calif.

[73] Assignees: The Rockefeller University, New York, N.Y.; Scripps Research Institute, LaJolla; Ciphergen Biosystems, Inc., Palo Alto, both of Calif.

[21] Appl. No.: 474,997

[22] Filed: Jun. 7, 1995

Related U.S. Application Data

[63] Continuation-in-part of Ser. No. 446,208, May 19, 1995, abandoned, which is a continuation-in-part of Ser. No. 341,555, filed as PCT/US93/05070 May 27, 1993, which is a continuation of Ser. No. 891,177, May 29, 1992, abandoned.

[51] Int. Cl.[6] .................... G01N 33/00; C12P 21/06; A61K 38/06; G03C 1/52
[52] U.S. Cl. .................... 436/89; 435/70; 435/68.1; 435/69.1; 530/333; 436/173
[58] Field of Search .................... 435/91.1, 70, 68, 435/69.1; 436/89, 173; 530/333

[56] References Cited

U.S. PATENT DOCUMENTS

| | | | |
|---|---|---|---|
| 5,045,694 | 9/1991 | Beavis et al. | 250/287 |
| 5,118,937 | 6/1992 | Hillenkamp et al. | 250/282 |
| 5,221,518 | 6/1993 | Mills | 422/62 |
| 5,281,538 | 1/1994 | Cottrell et al. | 436/173 |
| 5,288,644 | 2/1994 | Beavis et al. | 436/94 |

FOREIGN PATENT DOCUMENTS

| | | |
|---|---|---|
| 529 604 A1 | 3/1993 | European Pat. Off. |
| 38216481 | 9/1988 | Japan |
| WO 93/24835 | 12/1993 | WIPO |
| WO 94/06017 | 3/1994 | WIPO |

OTHER PUBLICATIONS

Roncari et al. Int J. of Prot res 1: 45–61, 1969.
Mizusawa et al. Appl 17: 366–71, 1969.
Minagawa et al. Agric Biol Chem 52: 1755–63, 1988.
Raaschou–Nielsen et al. (1994) *Peptide Research* 7:132–135. "Improvement of the Applicability of Carboxypeptidase Y in Peptide Synthesis by Protein Engineering".
Tsugita et al. (1992) *Eur. J. Biochem.* 206:691–696. "C–terminal sequencing of protein: A novel partial acid hydrolysis and analysis by mass spectrometry".
Tsugita et al. (1992) *Chemistry Letters* pp. 235–238. "Reaction of Pentafluoropropionic Anhydride Vapor on Polypeptide as Revealed by Mass Spectrometry. A Carboxypeptidase Mimetic Degradation".
Chait et al. (1992) The 40th ASMS Conference, Jun. 5, 1992, pp. 1939–1940, volume # not relevant. "A New Approach For Sequencing Peptides and Proteins".
Beavis et al. (1992) *Organic Mass Spectrometry,* 27:156–158. "α–Cyano–4–hydroxycinnamic Acid as a Matrix for Matrix–assisted Laser Desorption Mass Spectrometry".
Aebersold et al. (1992) *Protein Science,* 1:494–503. "Design, synthesis, and characterization of a protein sequencing reagent yielding amino acid derivatives with enhanced detectability by mass spectrometry".

(List continued on next page.)

Primary Examiner—W. Gary Jones
Assistant Examiner—Dianne Rees
Attorney, Agent, or Firm—Townsend and Townsend and Crew LLP

[57] ABSTRACT

Methods of producing biopolymer ladders and their use to obtain structural information about the biopolymer. The ladders are produced by setting up catalytic cleavage and terminating reactions at the end of biopolymer molecules. The terminating reactions terminate cleavage of a percentage of the biopolymer molecules at each round of cleavage.

51 Claims, 3 Drawing Sheets

OTHER PUBLICATIONS

Schnolzer et al. (1992) *Int. J. Peptide Protein Res.,* 40:180–193. "In situ neutralization in Boc–chemistry solid phase peptide synthesis".

B. Chait and S. Kent, (1992) *Science,* 257:1885–1894. "Weighing Naked Proteins: Practical, High–Accuracy Mass Measurement of Peptides and Proteins".

Hillenkamp et al. (1991) *Anal. Chem.,* 63:1193–1202. "Matrix–Assisted Laser Desorption/Ionization Mass Spectrometry of Biopolymers".

R. Beavis and B. Chait, (1990) *Anal. Chem.,* 62:1836–1840. "High–Accuracy Molecular Mass Determination of Proteins Using Matrix–Assisted Laser Desorption Mass Spectrometry".

R. Beavis and B. Chait (1990) *PNAS* 87:6873–6877. "Rapid, sensitive analysis of protein mixtures by mass spectrometry".

R. Beavis and B. Chait, (1989) *Rap. Comm. Mass Spec.,* 3:233. "Factors Affecting the Ultraviolet Laser Desorption of Proteins".

R. Beavis and B. Chait, (1989) The 37th ASMS Conference, Miami Beach, FL, May 21–26, 1989, pp. 1186–1187. "Matrix Assisted UV Laser Desorption Of Biologically Interesting Molecules".

Noren et al. (1989) *Science* 244:182–188. "A General Method for Site–Specific Incorporation of Unnatural Amino Acids into Proteins".

S.H. Kent (1988) *Annual Rev. biochem.* 57:957–984. "Chemical Synthesis of Peptides And Protins".

Karas et al. (1987) *International Journal Of Mass Spectrometry and Ion Processes,* 78:53–68. "Matrix–Assisted Ultraviolet Laser Desorption Of Non–Volatile Compounds".

Chait et al. Methods In Protein Sequence Analysis 1986, ed. K.A. Walsh, The Humana Press, 1987, pp. 483–492. "Mass Spectrometric Characterization Of Microscale Enzyme Catalyzed Reactions Of Surface–Bound Peptides And Proteins".

Karas et al. (1985) *Anal. Chem.,* 57:2935–2939. "Influence of the Wavelength in High–Irradiance Ultraviolet Laser Desorption Mass Spectrometry of Organic Molecules".

R. Self and A Parente (1983) *Biomedical Mass Spectrometry,* 10:78–82. "The Combined Use of Enzymatic Hydrolysis and Fast Atom Bombardment Mass Spectrometry for Peptide Sequencing".

J.D. Watson et al. (1983) Recombinant DNA—A Short Course, W.H. Freeman and Co., New York, pp. 61–63. "Restriction Fragments Lead to Powerful New Methods for Sequencing DNA".

L.A. Smith, R.M. Caprioli (1983) *Biomed. Mass Spectrom.* 10:98. "Following Enzyme Catalysis in Real–time Inside a Fast Atom Bombardment Mass Spectrometer".

Tsugita et al. (1982) *FEBS* 137:19–24. "Exopeptidase Digestion In Combination With Field Desorption Mass Spectrometry For Amino Acid Sequence Determination".

B. Chait and K. Standing (1981) *Int. J. Mass Spectrom., Ion Phys.* 40:185. "A Time–Of–Flight Mass Spectrometer For Measurement Of Secondary Ion Mass Spectra".

Lubert Stryer (1981) Biochemistry, 2nd Ed., W.H. Freeman and Co., New York, p. 663. Chapter 27: Protein Synthesis.

G.E. Tarr (1977), *Methods Enzymology* 47:355. "Improved Manual Sequencing Methods".

Mamyrin et al. (1973) *Sov. Phys. JETP* 37:45. "The mass–reflection, a new nonmagnetic time–of–flight mass spectrometer with high resolution".

William Konigsberg (1972) *Methods in Enzymol.* 25:326–332. "Subtractive Edman Degradation".

F. Richards and R. Lovins (1972) *Methods in Enzymol.* 25:314–325. "Mass Spectroscopy of Methylthiohydantoin Amino Acids: Identification, Quantitation, and the Analysis of Mixtures".

Walter A. Schroeder (1972) *Methods in Enzymol.* 25:298–313. "Degradation of Peptides by the Edman Method with Direct Identification of the Phenylthiohydantoin–Amino Acid".

Lee et al. (1994) *Biosci. Biotech. Biochem.* 58:1490–1495. Carboxypeptidase Taq, a Thermostable Zinc Enzyme, from Thermus aquaticus YT–1: Molecular Cloning, Sequencing, and Expression of the Encoding Gene in *Escherichia coli.*

Sakamoto (1994) *Biosci. Biotech. Biochem.* 58:1675–1678. Spectrophotometric Assay of Aminopeptidase with Thermostable Alanine Dehydrogenase from *Bacillus stearothermophilus.*

Chapotchartier (1994) *Eur. J. Biochem.* 224:497–506. Gene cloning and characterization of PepC, a cysteine aminopeptidase from *Streptococcus thermophilus,* with sequence similarity to the eucaryotic bleomycin hydrolase.

Midwinter (1994) *J. Appl. Bacteriol.* 77:288–295. Aminopeptidase N from *Streptococcus salivarius* subsp. thermophilus NCDO 573: purification and properties.

Hanner et al. (1990) *Biochem. et Biophys. Acta* 1033:148–153. Isolation and characterization of an intracellular aminopeptidase from the extreme thermophilic archaebacterium *Sulfolobus solfataricus.*

Jue, Diss Abstr. 45:1661, 1984.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Asp  Arg  Val  Tyr  Ile  His  Pro  Phe  His  Leu  Leu  Val  Tyr  Ser
1                   5                        10
```

METHODS FOR PRODUCING AND ANALYZING BIOPOLYMER LADDERS

This application is a continuation-in-part of Ser. No. 08/446,208, filed May 19, 1995 now abandoned, which is a continuation-in-part of Ser. No. 08/341,555, filed Nov. 23, 1994, filed from International application PCT/US93/05070, which is a continuation of from U.S. Ser. No. 07/891,177, filed May 29, 1992, now abandoned.

This invention was made with government support under grants RR00862 and GM38724 awarded by The National Institutes of Health. The government may have certain rights in the invention.

BACKGROUND OF THE INVENTION

The present invention relates to the field of biochemistry. In particular, it relates to methods of creating biopolymer ladders useful for obtaining structural information about the biopolymer, among other things.

The analysis of the structure of various biopolymers is an area of great importance in biochemistry. Molecular genetics depends on a knowledge of the nucleotide sequence of DNA or RNA molecules. The amino acid sequence of proteins provides information useful for studying their function and for isolating the nucleic acids that encode them. There is an increasing recognition of the importance of post-translational protein modifications in the coordination and control of biological processes at the molecular level. In particular, many cellular processes, including cell division, are controlled by selective and reversible phosphorylation of proteins. More recently, as carbohydrates have proven to be of importance in various biological functions, their structure has become a focus of attention. Various artificial polymers are also being developed to mimic the function of the natural biopolymers.

Various strategies exist for analyzing the structure of biopolymers. The most commonly used method of determining the sequence of nucleic acids, the dideoxy method, involves creating four sets of sub-sequences of a DNA molecule that terminate at each of the four bases, separating the fragments by polyacrylamide gel electrophoresis (PAGE), and using autoradiography to read out the sequence. By contrast, analysis of carbohydrate structure involves a laborious process of repetitively cleaving monosaccharides from a polysaccharide, and determining the identity of each monosaccharide removed.

A commonly used method of peptide sequencing, Edman degradation, involves sequentially cleaving amino acids from the amino-terminus of a peptide, and then determining the identity of the amino acid cleaved. However, traditional Edman degradation gives no information concerning post-translational modification of polypeptides. Additionally, Edman degradation cannot be used for C-terminal sequencing. Such information is crucial for correlating gene structure and protein function.

Peptide sequencing has also been attempted using exopeptidases to remove terminal amino acids from a polypeptide. Such methods involve removing samples of the polypeptide during the time course of digestion, terminating the action of the exopeptidase, and analyzing the resulting collection of samples. However, confusion can result from the widely varying rates at which the enzyme cleaves the peptide bond between different amino acids, which can cause gaps in the collection of peptides produced.

SUMMARY OF THE INVENTION

The present invention provides, for example, methods for producing a biopolymer ladder. In a first step, an ensemble of biopolymer molecules is contacted with a terminating reagent that reacts with the biopolymer molecules to add a terminating moiety, and with a cleavage reagent that catalyzes the removal of terminal units from the end of a biopolymer. According to one aspect of the invention, the rate of removing terminal units from biopolymer molecules bearing a terminating moiety is less than the rate of removing terminal units from biopolymer molecules that do not bear a terminating moiety. The biopolymers are contacted with the reagents under conditions and in amounts so as to create a collection of biopolymers comprising a nested set.

According to certain embodiments of this invention, the biopolymer is a polypeptide, the cleavage reagent is a carboxypeptidase, the terminating reagent is an amino acid amide, and the rate at which amino acids are removed from the polypeptide is faster than the rate at which the amino acid amide is added to the polypeptide. In certain embodiments, the cleavage reagent is thermostable.

This invention also provides biopolymer ladders comprising a nested set of at least two and preferably at least three biopolymer molecules wherein the members bear the same terminating moiety added catalytically.

This invention also provides methods of obtaining information about the structure of a biopolymer involving preparing a biopolymer ladder according to the methods of this invention, determining the differences in mass between the members of the ladder, and determining the identity of units whose masses correlate with the determined mass differences. According to one embodiment of the invention, the biopolymer is a polypeptide, the cleavage reagent cleaves a C-terminal or N-terminal peptide bond of polypeptides, thereby removing a terminal amino acid, and the method produces information about the sequence of amino acids in the polypeptide. According to another embodiment of this invention, the method of determining mass differences involves subjecting the biopolymer ladder to mass spectrometry analysis.

DETAILED DESCRIPTION OF THE INVENTION

This invention provides a method for the generation of biopolymer ladders via controlled digestion of a formed polypeptide using a catalytic agent. Biopolymer ladders are useful for obtaining structural information about the parent biopolymer. In one embodiment of the invention, the biopolymer ladder is composed of nested fragments of a parent biopolymer (optionally including the parent) that differ in length by one monomer unit each. These ladders are useful for determining the sequence of units in the parent biopolymer by, for example, determining the difference in mass between adjacent members of the ladder. The difference corresponds to, and aids in the identification of, the unit removed to produce the shorter fragment.

The methods of this invention involve setting up competing reactions directed to the terminus of the biopolymer molecules. One reaction is the removal of terminal units from the biopolymer molecules by a cleavage reagent, such as the hydrolysis of a terminal amino acid from a peptide by an exopeptidase. The other reaction is the reaction of the biopolymer molecules with a terminating reagent that results in addition of a terminating moiety to the biopolymer. The reactions are selected so that the rate for removing a terminal unit or units from biopolymers bearing a terminating moiety is slower than the rate for removing a terminal unit or units from biopolymer molecules that do not have terminating moieties. Thus, once a terminating moiety has been added to a biopolymer by reaction with the terminating reagent, the modified terminal unit is essentially refractory to cleavage by the cleavage reagent.

One embodiment of this invention takes advantage of the fact that catalysts lower the activation energy for reactions in both directions, bringing the system to an equilibrium defined by the relative concentration and chemical potentials of the reactants. In this embodiment, the terminating reagent is added to the system in molar excess, so that the equilibrium of the reaction of adding or removing the terminating moiety to or from the biopolymer is significantly in the direction of adding the terminating moiety. When the system is properly optimized, for any particular fragment size a terminating moiety is added to some fraction of the biopolymers and a terminal unit or units are cleaved from some other fraction. Those biopolymer fragments that are capped with a terminating moiety tend to resist further cleavage. Those that are not capped will be available for cleavage and subsequent capping. By allowing this reaction to proceed, a set of truncated fragments of the starting biopolymer is formed with the members of the set differing in composition by the same number of monomer units.

As used herein, the term "biopolymer" means a polymer made of a sequence of biochemical monomer units. Biopolymers include, for example, peptides, nucleic acids, complex carbohydrates, including analogs of these biopolymers, as well as other products of the sequential addition of biochemical monomer units. This includes, for example, peptides containing D- or L-amino acids, amino acid analogs and peptidomimetics that induce alpha helices, beta- or gamma-turns or other structural elements and nucleic acids containing nucleotide analogs.

As used herein, the term "biopolymer ladder" means a nested set of at least two and preferably, at least three, biopolymer molecules. As used herein, a "nested set" means a set in which the sequence of units of each member in the nested set, except, of course, the largest member, is contained in the sequence of a larger member in the set. The difference in size between any members of a nested set normally equals the number of terminal units removed in a single cleavage reaction. When the set contains at least three members, and the size of each member in the set differs from the next largest member by the same number of terminal units. For example, a biopolymer ladder created from a biopolymer with the sequence A-B-C-D-E-F-G-H-I, could include, for example, the nested set of biopolymers: A-B-C-D-E-F-G-H-*, A-B-C-D-E-F-G-*, A-B-C-D-E-F-*, A-B-C-D-E-*, A-B-C-D-*, and A-B-C-*. ("*" indicates a terminating moiety.) In this set, the biopolymers differ in length by one biopolymer unit. Another example of a biopolymer ladder created by the action of a cleavage reagent that removes two terminal units at a time from the biopolymer could be, for example, A-B-C-D-E-F-G-*, A-B-C-D-E-* and A-B-C-*. In this set, the biopolymers differ in length by two units. In the case of a branched biopolymer, such as a complex carbohydrate, a sequence is contained in another sequence if the structure of the larger branched structure is the same as the smaller branched structure except for at least one terminal unit, e.g., a terminal sugar moiety.

As used herein, the term "cleavage reagent" means a reagent containing a catalytic activity capable of catalyzing the removal of monomer units from a biopolymer. In one embodiment of the invention, the cleavage reagent is an enzyme. Other cleavage reagents include, for example, acids, bases, or naturally occurring products. The cleavage reagent can catalyze the removal of a single unit or multiple units from the end of the biopolymer.

When the biopolymer is a peptide the cleavage reagent can include, for example, exopeptidases, i.e., carboxypeptidases or aminopeptidases. Useful exopeptidases include mono-peptidases and poly-peptidases, such as di-peptidases and tri-peptidases. This invention contemplates, in particular, the use of carboxypeptidase Y, carboxypeptidase P, carboxypeptidase A and carboxypeptidase B. It also contemplates the use of aminopeptidases, such as leucine aminopeptidase, microsomal peptidase, and so forth.

Certain peptidases catalyze the breaking of the peptide bond between certain amino acids faster than the peptide bond between other amino acids. For example, carboxypeptidase A cleaves the peptide bond between a carboxylterminal proline and other amino acids (i.e., $NH_2$—$AA_1$— ... —$AA_n$—Pro—COOH) much more slowly than the peptide bond between other amino acids at the carboxyterminus. Therefore, in certain embodiments of the invention, the cleavage reagent can be a cocktail, including more than one peptidase, each with different specificities so that the rate of cleavage of peptide bonds is more uniform than the rate using any one of the cleavage reagents alone. One example of this is the use of a mixture of carboxypeptidase A and carboxypeptidase Y to produce a peptide ladder in which all the members of the nested set of fragments are represented.

Proteins and other biopolymers can have secondary or tertiary structure that leaves the terminal residues unaccessible to the cleavage reagent. Accordingly, this invention provides means and methods for exposing the termini of biopolymer molecules to allow the cleavage reagent access to the termini, for example, by denaturing the biopolymer molecules. One embodiment of this invention involves contacting the ensemble of biopolymer molecules with a thermostable cleavage reagent. As used herein, the term "thermostable cleavage reagent" refers to a cleavage reagent having an optimal activity at a temperature above 50° C. In this method, the ensemble of biopolymer molecules is contacted with the cleavage reagent at a temperature that will at least partially denature the biopolymer molecule, for example by disrupting secondary and/or tertiary structure. For many proteins, one can adequately denature the molecule so as to expose a terminus by exposing the molecules to temperatures above about 70° C. Normally, reactions will be carried out below about 100° C. However, the temperature can be chosen with reference to the optimal reaction temperature of the cleavage reagent. For example, a reaction temperature of 90° C. may be preferable in the case of a thermostable enzyme whose optimal reaction temperature is 90° C.

Thermostable enzymes such as those found in thermophilic bacteria are useful in this invention. Several thermostable carboxypeptidases have been identified in and isolated from thermophilic bacteria. For example, carboxypeptidase Taq, found in *Thermus aquaticus* YT-1, has an optimum reaction temperature of 80° C. (S.-H. Lee et al. (1994) *Biosci. Biotech. Biochem.* 58:1490–1495.) Thermostable aminopeptidases have been identified in and isolated from *Bacillus stearothermophilus* (Y. Sakamoto (1994) *Biosci. Biotech. Biochem.* 58:1675–1678); *Streptococcus thermophilus* (M. P. Chapotchartier (1994) *Eur. J. Biochem.* 224:497–506); *Streptococcus salivarius* subsp. *thermophilus* (amino peptidase N) (R. G. Midwinter (1994) *J. Appl. Bacteriol.*, 77:288–295); and *Sulfolobus solfataricus* (M. Hanner et al. (1990) *Biochem. et Biophys. Acta* 1033:148–153).

It will be clear to anyone skilled in the art that other cleavage reagents having desirable properties can be isolated from organisms living in extreme environments and used in the methods of this invention. For example, salt-tolerant cleavage reagents can be isolated from halophilic bacteria or archeabacteria. Salt-tolerant cleavage reagents are useful for preparing biopolymer ladders from biopolymers, especially proteins, that are denatured under high ionic strength conditions.

In the case of nucleic acids, the cleavage reagent can include, for example, 3' or 5' exonucleases such as Bal-31 nuclease, *E. coli* exonuclease I, *E. coli* exonuclease VII, *E. coli* DNA polymerase I exonuclease activity, the exonuclease activity associated with Klenow fragment of DNA polymerase I, an exonuclease activity associated with T4 coliphage DNA polymerase, and so on.

In the case of carbohydrates, the cleavage reagent can include, for example, exoglycosidases such as a variety of fucosidases, mannosidases, galactosidases and so forth.

As used herein, the term "terminating reagent" means a reagent that, upon reaction with a biopolymer, adds a "terminating moiety" to the biopolymer that slows or prevents the reaction of the cleavage reagent with the biopolymer. That is, the reaction for removing a terminal unit or units from a biopolymer bearing a terminating moiety is slower than the reaction rate for removing a terminal unit or units from a biopolymer molecule that has not reacted with a terminating moiety. When the cleavage reagent is an enzyme, the maximum velocity for removing terminal units from a biopolymer bearing a terminating moiety is slower than the maximum velocity for removing a terminal unit from a biopolymer not having a terminating moiety.

In one embodiment of this invention, the cleavage reagent catalyzes both the cleavage of terminal units and the addition of the terminating moiety, e.g., when the cleavage reagent is an enzyme. In this case, the terminating reagent can be selected to have a structure sufficiently different from the original units of the biopolymer that the rate constant for adding/removing the terminating reagent is slower that for adding/removing the original units. According to a preferred embodiment of the invention, the rate at which non-terminated units are removed from the biopolymer molecules is greater than the rate at which terminating moieties are added to terminal units of biopolymer molecules.

For example, in the case of peptides in which the cleavage reagent includes a carboxypeptidase, the terminating reagent can be an amino acid amide. L-lysinamide has at least two desirable properties as a terminating reagent for use in peptide ladder generation. First, L-lysinamide is highly water soluble. This allows its use at high molar concentration. Secondly, L-lysinamide contains a basic moiety and, therefore, may enhance peptide ladder detection when the means to be used for analyzing the peptide is MALDI mass spectrometry because basic groups can aid in ionization. Because the amino acid amides have amide groups in place of carboxyl groups, carboxypeptidases catalyze their addition/removal from the carboxy-terminus of a peptide at rates several orders of magnitude less than ordinary amino acids. For example, carboxypeptidase Y catalyzes the hydrolysis of C-terminal peptide bonds of peptides at rates up to three orders of magnitude greater than for terminal amides when comparing the kcat/KM for the hydrolysis of FA-Phe-Leu-OH and FA-Phe-Gly-NH$_2$ (Raaschou-Nielsen et al. (1994) *Peptide Research* 7:132–135). Thus, for all practical purposes, once an amino acid amide is added to the carboxy-terminus of a peptide, the carboxypeptidase will not remove it as it continues to cleave terminal amino acids from other peptide molecules.

When the cleavage reagent is an amino peptidase, the terminating agent can be an n-acetyl amino acid, such as n-acetyl lysine.

In a variation of these methods, the terminating reagent can include a mixture of isotopes. Biopolymer ladders containing such mixtures are useful in detecting members of the ladder. For example, members of the ladder bearing termination moieties that differ in mass can be identified by split peaks in mass spectrometry (W. R. Gray (1970) *Biochem. Biophys. Res. Commun.* 41:1111–1119). Members of ladders bearing radioactively labelled terminating moieties also can be identified by autoradiography.

Methods of producing biopolymer ladders involve optimizing the reaction system by using appropriate amounts of the reagents and selecting reaction conditions so as to form a ladder. This involves using a sufficient amount of terminating reagent so as to produce a detectable amount of terminated biopolymer at each sequential cleavage step. This amount depends, of course, on the sensitivity of the detection means selected. Typically, the terminating reagent is added in molar excess so as to significantly drive the reaction in the direction of adding terminating moieties. According to one embodiment, terminating reagent is added in an amount so that several percent of the biopolymers are terminated in each reaction. A range of useful amounts of ladder members can easily be determined empirically.

Other factors that can be modulated to set appropriate conditions include temperature, pH, and buffer system. Generally speaking, when the cleavage reagent is an enzyme, conditions under which the enzyme would normally be used will provide a good starting point for further optimizing of reaction conditions. Additionally, in the case that a cocktail of enzymatic cleavage reagents is to be used, it is useful to select compatible enzymes. Taking pH as an example, in many cases it will be useful to select enzymes which have similar activity profiles as a function of pH, however there may be cases in which it is desirable to use an enzymatic cleavage reagent at less than its optimal pH in order to control substrate preference effects.

The biopolymers subjected to the methods of this invention can have a variety of sizes. However, the impact of the average uncertainty in measured mass becomes more significant as the molecular mass increases. Below 3500 daltons, the mass deviation is less than ±0.3 dalton, and there is no ambiguity in distinguishing even the most closely related pairs of monomers and, in particular, amino acids (Leu/Ile have identical mass). However, above 3500 daltons, uncertainties of 0.4 to 0.9 dalton introduce certain ambiguities in the identification of monomers of closely similar residue masses. For polypeptides that do not contain any amino acids having similar mass to other amino acids, this uncertainty will cause no problem at all. Even if there is some ambiguity in the identity of certain monomers in the polymer, the method of the invention still provides useful sequence information. Accordingly, in certain embodiments of the invention, the biopolymer has mass below about 5 kDa and, preferably, below about 3.5 kDa. When the biopolymer is a polypeptide, the polypeptide can have fewer than about 50 amino acids and, preferably, fewer than about 35 amino acids. Valuable sequence information can be obtained from polypeptides having larger sizes, as well.

This invention also provides the biopolymer ladders produced by the methods of this invention. These ladders are characterized by a collection of biopolymers having at least two, and preferably three members in a nested set wherein the members bear the same terminating moiety. In particular, this invention is directed to ladders having a catalytically added terminating moiety such as, in the case of peptides, an amino acid amide such as lysinamide.

Biopolymer ladders can yield useful structural information about the biopolymer, including for example, the sequence of monomer units. When the cleavage reagent cleaves one unit from the biopolymer at a time, the members of the ladder will differ in mass by the mass of the unit removed, thereby providing information about the identity of the removed unit. Ladders created by the action of catalysts that remove more than one monomer unit from a biopolymer at a time also provide useful information. For example, digesting a protein with trypsin will leave either lysine or arginine at the carboxy-terminus. When the resulting peptide is digested with a di-peptidase in the methods of this invention, the mass of the first two units removed will equal the mass of arginine or lysine and the mass of the penultimate amino acid, thus helping to yield its identity. The identity of several amino acids at either end of a protein often will suffice to prepare primers for PCR useful in amplifying a gene encoding the protein. Even incomplete sequence information can supplement information from other sources.

Accordingly, this invention is also directed to methods of obtaining sequence information about a biopolymer. The methods involve preparing a biopolymer ladder comprising a collection of biopolymers in a nested set according to the methods of this invention, determining the differences in mass between the members, and determining the identity of units whose masses correlate with the determined mass differences. The difference in mass between members of the ladder aids in identifying the removed units.

According to one embodiment, this invention provides a method for determining the sequence of amino acids in a polypeptide. The method involves creating a polypeptide ladder having a nested set of peptides in which each of the peptides differs in length from another peptide in the set by one amino acid, determining the difference in mass between the peptides in the nested set, and determining the identity of amino acids whose masses correlate with the determined mass differences. The identity of the amino acids in the nested set indicates the sequence of amino acids in the peptide. This method does not require determining the amino acid sequence of the entire polypeptide. Partial sequences are also useful.

This invention contemplates several methods of determining mass differences between members of a biopolymer ladder. According to one embodiment of this invention, the mass differences between members of the ladder are determined by mass spectrometry. Methods for mass spectrometry include, for example, $^{252}$Cf plasma desorption, electrospray ionization, fast ion bombardment, chemical induction decay and, in particular, matrix-assisted laser desorption mass spectrometry ("MALDI-MS"). Methods of performing mass spectrometry on biomolecules are well known in the art.

Apparati and methods for performing MALDI-MS are described in International Publication WO 93/24835 (U.S. patent application Ser. No. 08/341,555), U.S. Pat. No. 5,288,644, R. Beavis and B. Chait (1990) *PNAS* 87:6873–6877, B. Chait and K. Standing (1981) *Int. J. Mass Spectrom, Ion Phys.* 40:185 and Mamyrin et al. (1973) *Sov. Phys. JETP* 37:45, all incorporated herein by reference for all purposes. Briefly, the frequency tripled output of, e.g., a Q-switched Lumonics HY400 neodymium/yttrium aluminum garnet laser ("Nd-YAG") (355 nm, 10-nsec output pulse) is focused by a lens (12-inch focal length) through a fused silica window onto a sample inside the mass spectrometer. The product ions formed by the laser are accelerated by a static electric potential of 30 kV. The ions then drift down a 2-m tube maintained at a vacuum of 30 µPa and their arrival at the end of the tube is detected and recorded using, e.g., a Lecroy TR8828D transient recorder. The transient records of up to 200 individual laser shots are summed together and the resulting histogram is plotted as a mass spectrum. Peak centroid determinations and data reduction can be performed using a VAX workstation or other computer system.

Protein samples can be prepared for laser desorption analysis by the following procedure. The laser desorption matrix material that preferably absorbs above 300 nm is dissolved in aqueous 30% (vol/vol) acetonitrile containing 0.1% (wt/wt) trifluoroacetic acid, to make a standard solution at 20° C. (≈50 mM). A preferred matrix is α-cyano-4-hydroxy cinnamic acid. A solution containing the protein sample of interest is then added to the matrix solution to give a final protein concentration of 0.1–10 µM. A small aliquot (0.5 µl) of this mixture is then applied to a flat metal probe tip (2-mm diameter) and dried at room temperature with forced air. The resulting deposit is washed in 4° C. distilled water by immersing the tip for 10 seconds. This washing step aids the removal of soluble ionic contaminants from the protein/matrix deposit, without removing the proteins or matrix. Once the sample is washed, it is inserted into the mass spectrometer and analyzed. The entire protocol, from the beginning of sample preparation to finished mass spectral analysis, takes about 15 minutes.

Another method useful for determining the difference in mass of members of biopolymer ladder is acrylamide gel electrophoresis.

EXAMPLE

Figure 1:
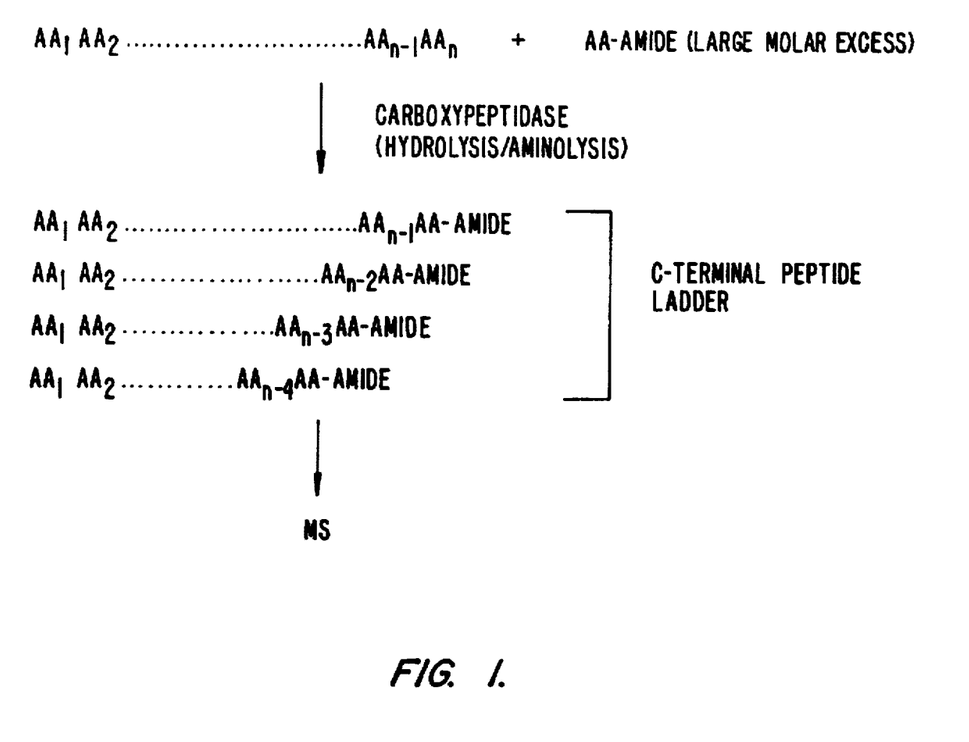
FIG. 1 illustrates the overall process of one embodiment of the invention.
Figure 2:
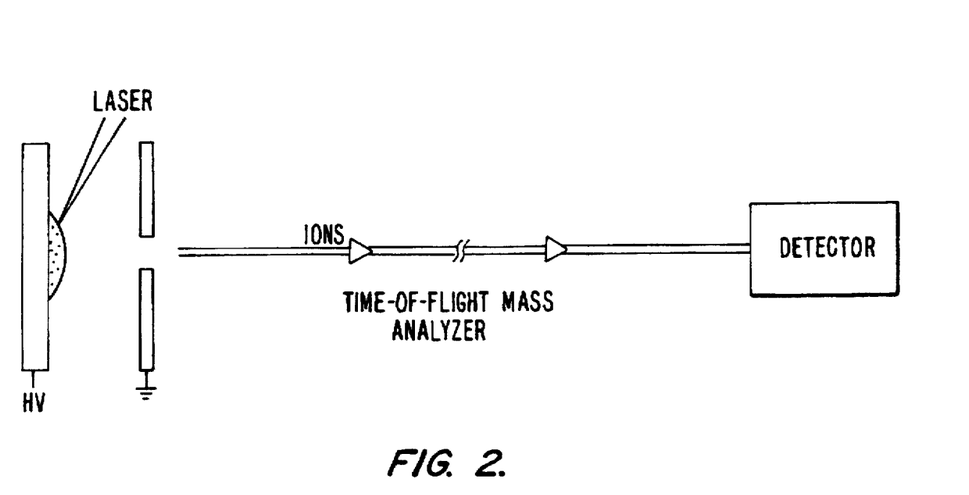
FIG. 2 illustrates a matrix-assisted laser desorption/ionization ("MALDI") time-of-flight mass spectrometer.
Figure 3:
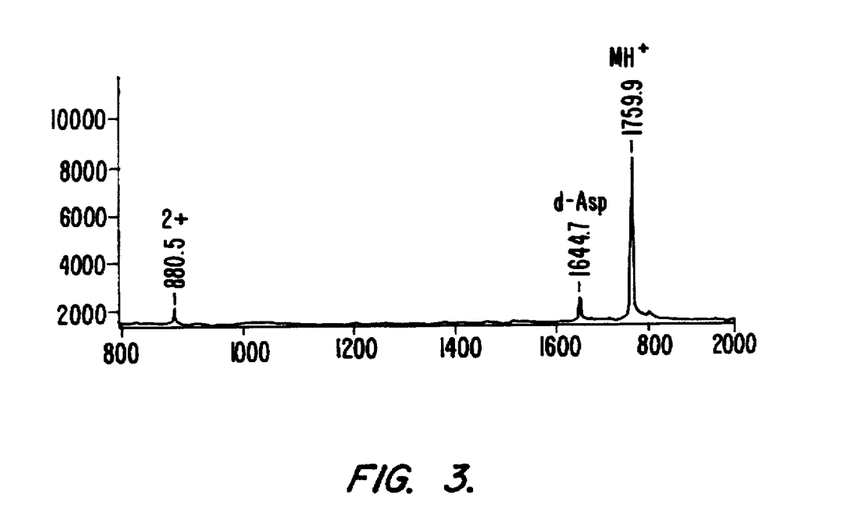
FIG. 3 shows the MALDI time-of-flight ("TOF") mass spectrum of synthetic porcine renin substrate.

We determined the sequence of synthetic porcine renin substrate tetradecapeptide (Sigma) using carboxypeptidase Y. The peptide has the amino acid sequence DRVYIHPFHL LVYS [SEQ ID NO:1] (using the one letter code for amino acid residues) and molecular weight of 1759.0 Da. FIG. 3 is the matrix-assisted laser desorption ionization mass spectrometric (MALDI-MS) spectrum of renin substrate tetradecapeptide. The MALDI-MS analysis was carried out on a laser desorption ionization time-of-flight mass spectrometer constructed at the Rockefeller University (R. Beavis and B. Chait (1990) *Anal. Chem.* 62:1836–1840). α-Cyano-4-hydroxycinnamic acid was used as the laser desorption matrix (Beavis et al. (1992) *Org. Mass Spectrom.* 27:156–158) in the form of saturated solution in water/acetonitrile (2:1, v/v). One µl of peptide solution was mixed with 5 μl of matrix solution. 0.5 μl of sample solution was then applied on the sample probe and analyzed (FIG. 3). In this spectrum, the singly (MH+) and doubly (2+) protonated molecular ions were observed at m/z 1759.9 and 880.5 amu. The peak denoted as "d-Asp" (at m/z 1644.7 amu) is an amino-terminal truncated peptide impurity.

The carboxy-terminal sequence of this peptide was obtained by using carboxypeptidase digestion in the presence of an excess amount of amino acid amide followed by or concurrently with matrix-assisted laser desorption ionization mass spectrometric data analysis (Hillenkamp et al. (1991) *Anal. Chem.* 63:1193–1202). The amino acid amide L-lysinamide was used to balance the fast digestion steps of the carboxypeptidase during the digestion and to eliminate the sequence gaps. The competitive carboxypeptidase Y sequencing reaction was carried out in the presence of an excess amount of lysinamide (1 M, L-Lysinamide dihydrochloride (Sigma)) at pH 7.5.

Figure 4:
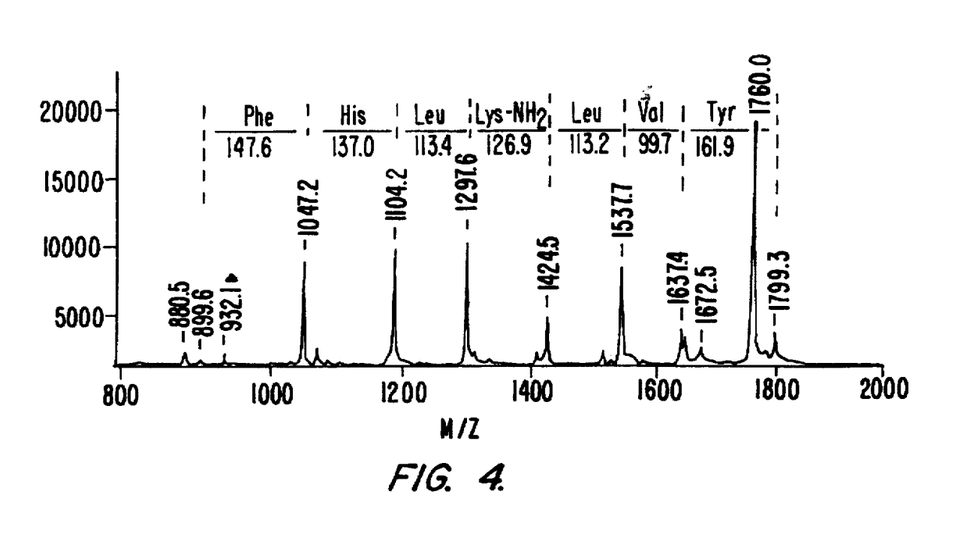
FIG. 4 shows the matrix-assisted laser desorption/ionization mass spectrometric ("MALDI-MS") spectrum of a peptide ladder of renin substrate tetradecapeptide made according to the methods of this invention.

Five μl of peptide substrate (1 mM) and 5 μl of carboxypeptidase Y (100 (g/ml) were incubated in the buffer solution (total volume 100 Al, consisting of 50 mM of Hepes, 5 mM of EDTA and 1M of lysinamide) at 37° C. for 20 minutes. The reaction was then stopped by adding 20 μl of 2% TFA to 10 μl of reaction solution. One μl reaction mixture solution was mixed with 5 μl MALDI matrix and 0.5 μl sample solution was analyzed by MALDI-MS. The resulting sequencing spectrum is shown in FIG. 4. The spectrum provides the carboxyl terminal sequence of up to seven amino acid residues of this polypeptide in a single operation.

The amino acid sequence was determined as follows. The first carboxy-terminal amino acid residue was determined by adding 127 Da (L-Lysinamide residue mass) to the mass of the intact molecular ion (1760 Da), to give 1887 Da, followed by subtraction of the highest mass of lysinamide modified peptide peak (1799.3 Da). This calculation gives a mass difference of 87.7 Da, which corresponds to a serine residue. The remaining carboxy-terminal sequence can be read out from the mass differences between adjacent peaks in the spectrum. The mass difference of 126.9 Da between the peaks at m/z 1424.5 and 1297.6 corresponds to the lysinamide. The peaks on the lower mass side of the lysinamide residue correspond to the unmodified peptides and the peaks on the higher mass side of lysinamide correspond to the lysinamide modified peptides.

Figure 5:
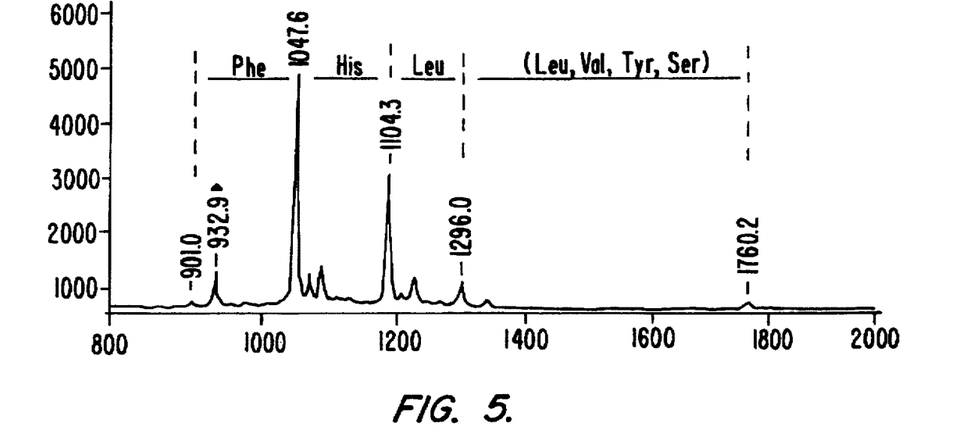
FIG. 5 shows a sequencing spectrum of synthetic porcine renin substrate subjected to carboxypeptidase digestion but without a terminating reagent.

For comparison, the same peptide was digested with carboxypeptidase Y in the absence of lysinamide. FIG. 5 shows the sequencing spectrum after 10 minutes reaction at 37° C. The spectrum contains several gaps which lack an intermediate member of the peptide ladder. These results clearly indicate that the method of this invention balances the fast hydrolysis reactions with the aminolysis reactions. As a result, the sequence gaps in the normal carboxypeptide Y digestion (FIG. 5) were filled up by the lysinamide modifications (FIG. 4).

L-Lysinamide is used as a nucleophile and competitive substrate for peptide substrate hydrolysis by carboxypeptidase Y, which decreases the hydrolysis rate. The aminolysis product generated by formation of lysinamide at the C-terminus of peptide can slow down the hydrolysis rate. This is shown by the large amount of intact peptide remaining (FIG. 4). This reduced rate of hydrolysis is not a disadvantage. It provides for more control of the degradation/ladder-forming process. The rate can be increased by the simple addition of more enzyme.

The present invention provides a substantially novel method for preparing biopolymer ladders. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for producing a polypeptide ladder comprising contacting an ensemble of polypeptide molecules with
  (i) a terminating reagent that reacts with the polypeptide molecules to add terminating moieties and
  (ii) a cleavage reagent that removes terminal units from an end of the polypeptide molecules;
wherein the rate of removing terminal units from polypeptide molecules bearing a terminating moiety is less than the rate of removing terminal units from polypeptide molecules that do not bear a terminating moiety, the polypeptide molecules being contacted with the cleavage and terminating reagents under conditions and in amounts so as to create a collection of polypeptide molecules having at least two members in a nested set.

2. The method of claim 1 wherein the cleavage reagent catalyzes the addition of terminating moieties to the polypeptide molecules.

3. The method of claim 2 wherein the rate at which the cleavage reagent catalyzes removal of non-terminated units from the polypeptide molecules is greater than the rate at which it catalyzes the addition of terminating moieties.

4. The method of claim 3 wherein the cleavage reagent comprises an exopeptidase.

5. The method of claim 4 wherein the exopeptidase is a carboxypeptidase.

6. The method of claim 5 wherein the carboxypeptidase is carboxypeptidase A, carboxypeptidase P, carboxypeptidase Y or carboxypeptidase B.

7. The method of claim 4 wherein the exopeptidase is an aminopeptidase.

8. The method of claim 7 wherein the aminopeptidase is leucine aminopeptidase or microsomal peptidase.

9. The method of claim 4 wherein the exopeptidase is a poly-peptidase.

10. The method of claim 5 wherein the terminating reagent is an amino acid amide.

11. The method of claim 10 wherein the amino acid amide is L-lysinamide.

12. The method of claim 1 wherein the terminating reagent is isotopically-labeled.

13. The method of claim 1 wherein the cleavage reagent is thermostable.

14. The method of claim 13 wherein the cleavage reagent is a thermostable carboxypeptidase.

15. The method of claim 14 wherein the thermostable carboxypeptidase is carboxypeptidase Taq.

16. The method of claim 13 wherein the cleavage reagent is a thermostable aminopeptidase.

17. The method of claim 16 wherein the thermostable aminopeptidase is an aminopeptidase found in *Bacillus stearothermophilus*, *Streptococcus thermophilus*, *Streptococcus salivarius subsp. thermophilus*, or *Sulfolobus solfataricus*.

18. The method of claim 13 wherein the conditions comprise contacting the ensemble of polypeptide molecules with the thermostable cleavage reagent at a temperature between about 70° C. and about 100° C.

19. A polypeptide ladder comprising a collection of polypeptide molecules having at least two members in a nested set wherein the members bear the same terminating moiety and wherein the terminating moiety is added catalytically.

20. The polypeptide ladder of claim 19 having at least three members in a nested set.

21. The polypeptide ladder of claim 20 wherein the terminating moiety is an amino acid amide.

22. The polypeptide ladder of claim 21 wherein the terminating moiety is L-lysinamide.

23. The polypeptide ladder of claim 20 wherein the terminating moiety is an n-acetyl amino acid.

24. The polypeptide ladder of claim 23 wherein the n-acetyl amino acid is n-acetyl lysine.

25. A method of obtaining information about the structure of a polypeptide comprising the steps of:
(a) preparing a polypeptide ladder comprising a collection of polypeptide molecules having at least two members in a nested set according to the method of claim 1, (b) determining the differences in mass between the members, and (c) determining the identity of amino acid units whose masses correlate with the determined mass differences.

26. The method according to claim 25 wherein said step of determining differences in mass comprises the steps of depositing the polypeptide molecules in a matrix; and applying a laser to desorb the polypeptide molecules from the matrix.

27. A method of obtaining information about the sequence of amino acids in a polypeptide comprising the steps of:

a) preparing a polypeptide ladder by contacting an ensemble of polypeptides with
(i) a terminating reagent that reacts with the polypeptide molecules to add terminating moieties and
(ii) a cleavage reagent that cleaves a terminal peptide bond of polypeptides thereby removing a terminal amino acid; wherein the rate of removing terminal units from polypeptide molecules bearing a terminating moiety is less than the rate of removing terminal amino acids from polypeptides that do not bear a terminating moiety, the polypeptides being contacted with the cleavage and terminating reagents under conditions and in amounts so as to create a collection of polypeptides having at least two members in a nested set;

b) determining the differences in mass between the members; and c) determining the identity of amino acids whose masses correlate with the determined mass differences, whereby the order of mass differences in the polypeptide ladder indicates the identity of the amino acids and indicates the sequence of amino acids in the polypeptide.

28. The method of claim 27 wherein the cleavage reagent catalyzes the addition of terminating moieties to the polypeptide molecules.

29. The method of claim 28 wherein the rate at which the cleavage reagent catalyzes removal of non-terminated units from the polypeptide molecules is greater than a rate at which it catalyzes the addition of terminating moieties to terminal units of polypeptide molecules.

30. The method as recited in claim 29 wherein said cleavage reagent comprises a carboxypeptidase.

31. The method as recited in claim 30 wherein said terminating reagent comprises an amino acid amide.

32. The method as recited in claim 31 wherein said cleavage reagent comprises carboxypeptidase-Y and said terminating reagent comprises L-Lysinamide.

33. The method as recited in claim 29 wherein said cleavage reagent comprises a mixture of carboxypeptidases wherein rate of cleavage of peptide bonds is more homogenous among amino acids than the rate of cleavage using any one of the carboxypeptidases alone.

34. The method of claim 29 wherein the step of determining the differences in mass comprises subjecting the polypeptide ladder to mass spectrometry.

35. The method of claim 34 wherein the method of mass spectrometry is matrix-assisted laser desorption/ionization mass spectrometry.

36. The method of claim 34 wherein the polypeptide has a mass below about 5 kDa.

37. The method of claim 34 wherein the polypeptide has a mass below about 3.5 kDa.

38. The method of claim 27 wherein the cleavage reagent is thermostable.

39. The method of claim 38 wherein the cleavage reagent is a thermostable carboxypeptidase.

40. The method of claim 39 wherein the thermostable carboxypeptidase is carboxypeptidase Taq.

41. The method of claim 38 wherein the cleavage reagent is a thermostable aminopeptidase.

42. The method of claim 41 wherein the thermostable aminopeptidase is an aminopeptidase from *Bacillus stearothermophilus*, *Streptococcus thermophilus*, *Streptococcus salivarius subsp. thermophilus*, or *Sulfolobus solfataricus*.

43. The method of claim 38 wherein the conditions comprise contacting the ensemble of polypeptide molecules with the thermostable cleavage reagent at a temperature between about 70° C. and about 100° C.

44. The method of claim 1 wherein the collection has at least three members in a nested set.

45. The polypeptide ladder of claim 19 wherein each member of the nested set has an amino acid sequence selected from an amino acid sequence of a largest member of the nested set and wherein each member of the nested set bears the terminating moiety on an amino acid at a different position in the sequence.

46. The polypeptide ladder according to claim 19 having at least three members, wherein each member of the nested set differs in length by the same number of amino acid units.

47. The polypeptide ladder according to claim 45 having at least three members, wherein each member of the nested set differs in length by the same number of amino acid units.

48. The polypeptide ladder according to claim 47 wherein each member of the nested set differs in length by one amino acid.

49. The method of claim 19 wherein the collection has at least three members in a nested set.

50. The method of claim 25 wherein the collection has at least three members in a nested set.

51. The method of claim 27 wherein the collection has at least three members in a nested set.

* * * * *